United States Patent

[19]

Cho

[11] Patent Number: 6,019,601

[45] Date of Patent: Feb. 1, 2000

[54] TRAY MODELING SYSTEM WITH ARTICULATOR ASSEMBLY AND EJECTION MECHANISM FOR PRODUCING A DENTAL MODEL

[76] Inventor: Kyung Rok Cho, 22844 Cottage Ct. #104, Novi, Mich. 48375

[21] Appl. No.: 09/190,319

[22] Filed: Nov. 12, 1998

Related U.S. Application Data

[63] Continuation-in-part of application No. 09/133,231, Aug. 13, 1998, Pat. No. 5,913,681.

[51] Int. Cl.[7] .................................................... A61C 11/00
[52] U.S. Cl. ............................................... 433/60; 433/34
[58] Field of Search ................................. 433/34, 45, 60, 433/63, 69, 74

[56] References Cited

U.S. PATENT DOCUMENTS

| | | | |
|---|---|---|---|
| 2,619,725 | 12/1952 | Roeser | 433/60 |
| 3,581,398 | 6/1971 | Thomas | 433/34 |
| 3,916,524 | 11/1975 | Lystager | 433/60 |
| 4,030,197 | 6/1977 | Linck, II et al. | 433/60 |
| 4,200,981 | 5/1980 | Fine | 433/60 |
| 4,299,570 | 11/1981 | Yogosawa | 433/65 |
| 4,439,151 | 3/1984 | Whelan | 433/60 |
| 4,865,544 | 9/1989 | Scruggs | 433/64 |
| 5,197,874 | 3/1993 | Silva et al. | 433/74 |
| 5,306,145 | 4/1994 | Michael | 433/34 |
| 5,506,095 | 4/1996 | Callne | 433/60 |
| 5,622,497 | 4/1997 | Cho | 433/60 |
| 5,658,143 | 8/1997 | Kuperman | 433/60 |

Primary Examiner—John J. Wilson
Attorney, Agent, or Firm—Gifford, Krass, Groh, Sprinkle, Anderson & Citkowski, P.C.

[57] ABSTRACT

A system and articulator for use with a replication of a dental patient's teeth taken by a conventional dental impression in the creation of a dental model of the patient's mouth. A first tray and a second tray are provided, each tray including a base surface having at least one frangible portion formed therewith, first and second spaced apart and upwardly extending side walls and first and second end walls which define a recessed cavity therebetween. The side walls are each defined by pluralities of spaced apart and vertically extending raised portions which permit segmented portions of the upper and lower dental models to be releasably attachable in correct position. A template base is provided with a configuration suitable for supporting an underside of each of said trays in an upright fashion and includes at least one raised portion corresponding in location and placement with the at least one frangible portion. A punch member is configured to engage first and second selected surfaces of each of the trays and downwardly actuates the trays so that the frangible portions are forcibly disengaged from the base surface and the base layer of stone and associated dental model are ejected from within the recessed cavity. The articulator includes a first mounting portion extending from the first tray and a second identically shaped mounting portion extending from the second tray. A first insert portion engages the first mounting portion and a second insert portion engages the second mounting portion. The first and second insert portions are each adjustable in height relative to their associated trays and further include aligning eyelet portions which permit them to be hingedly secured along a common axis so as to provide for desired positioning of the opposingly arrayed dental models.

12 Claims, 4 Drawing Sheets

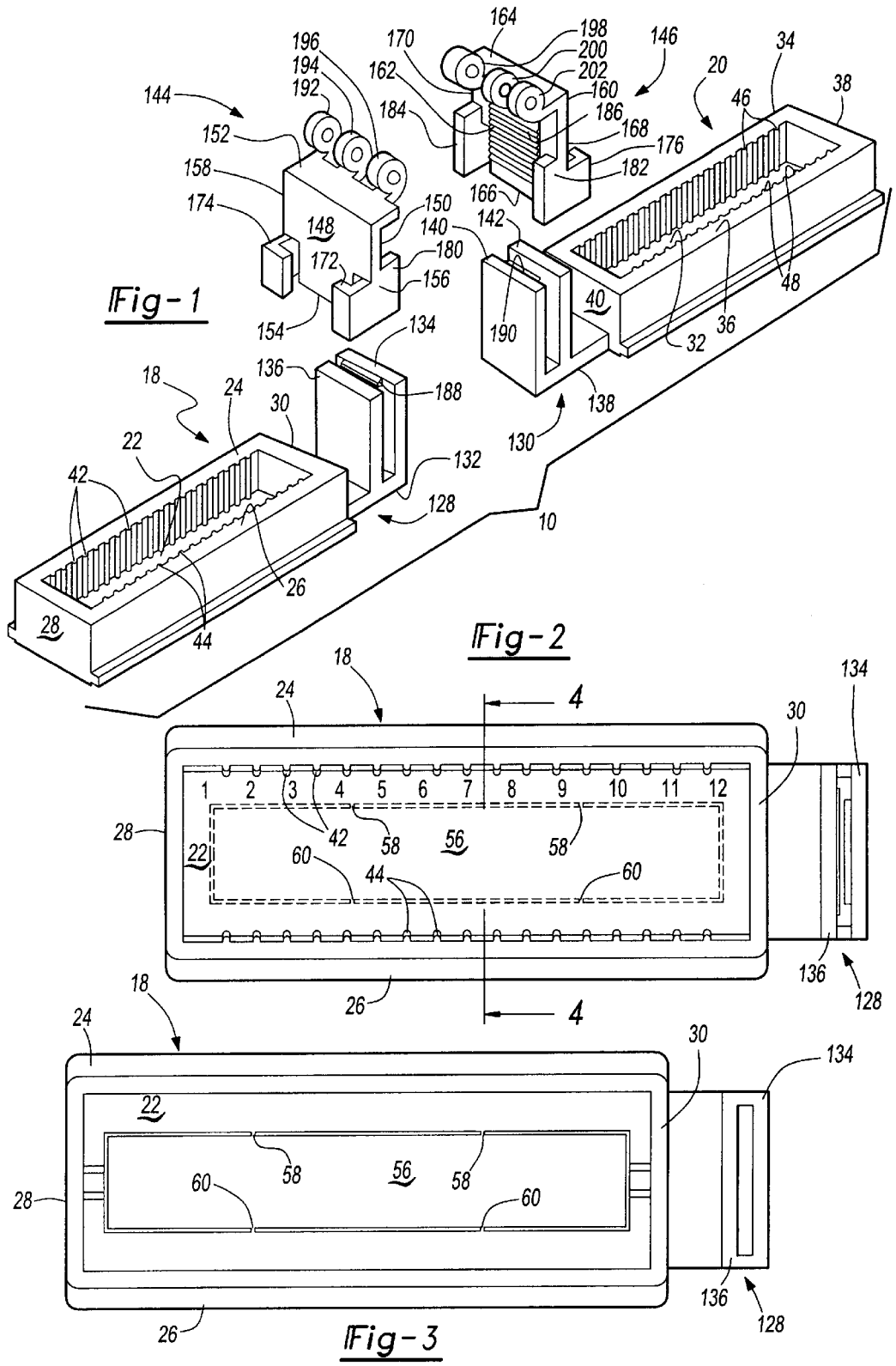

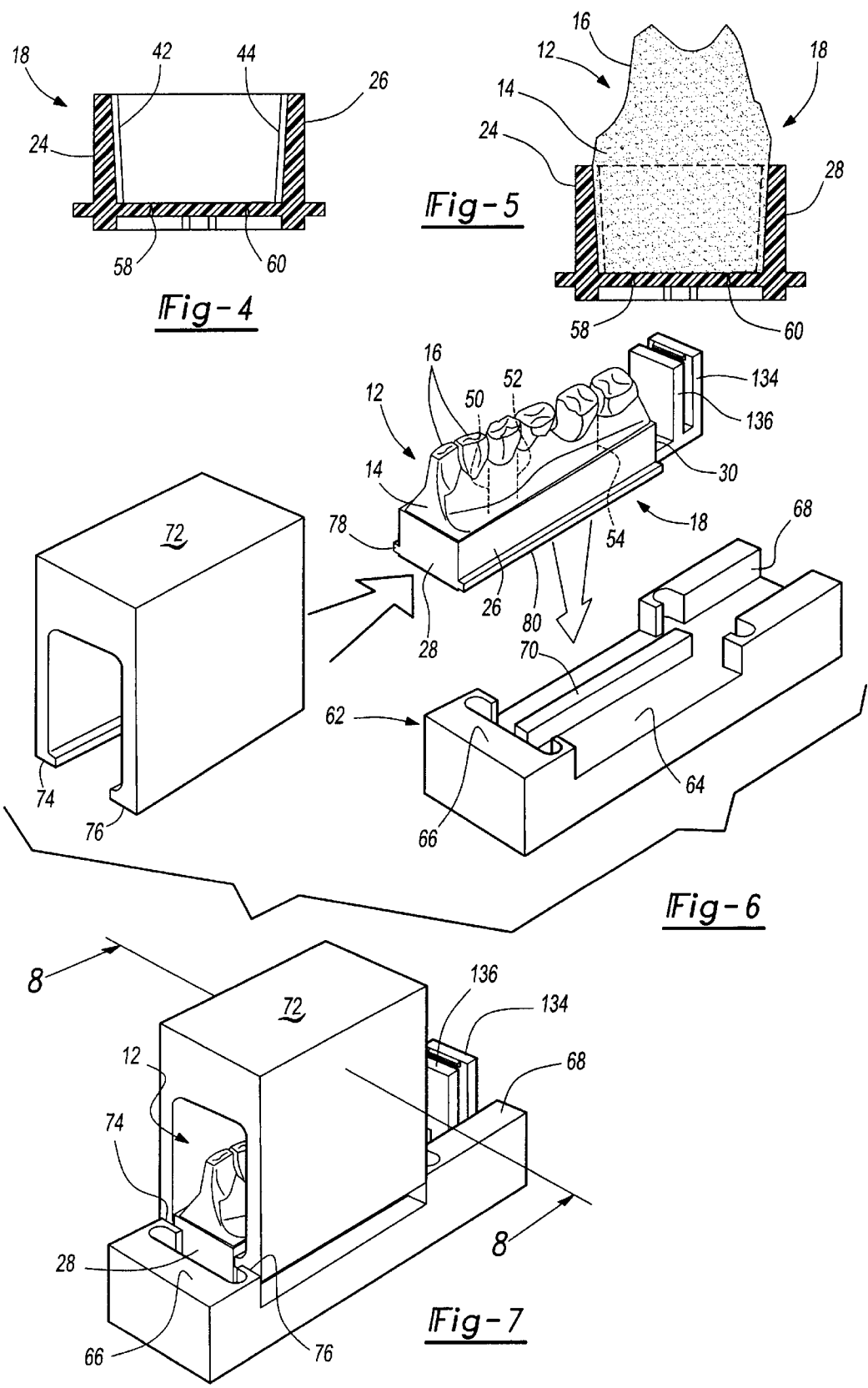

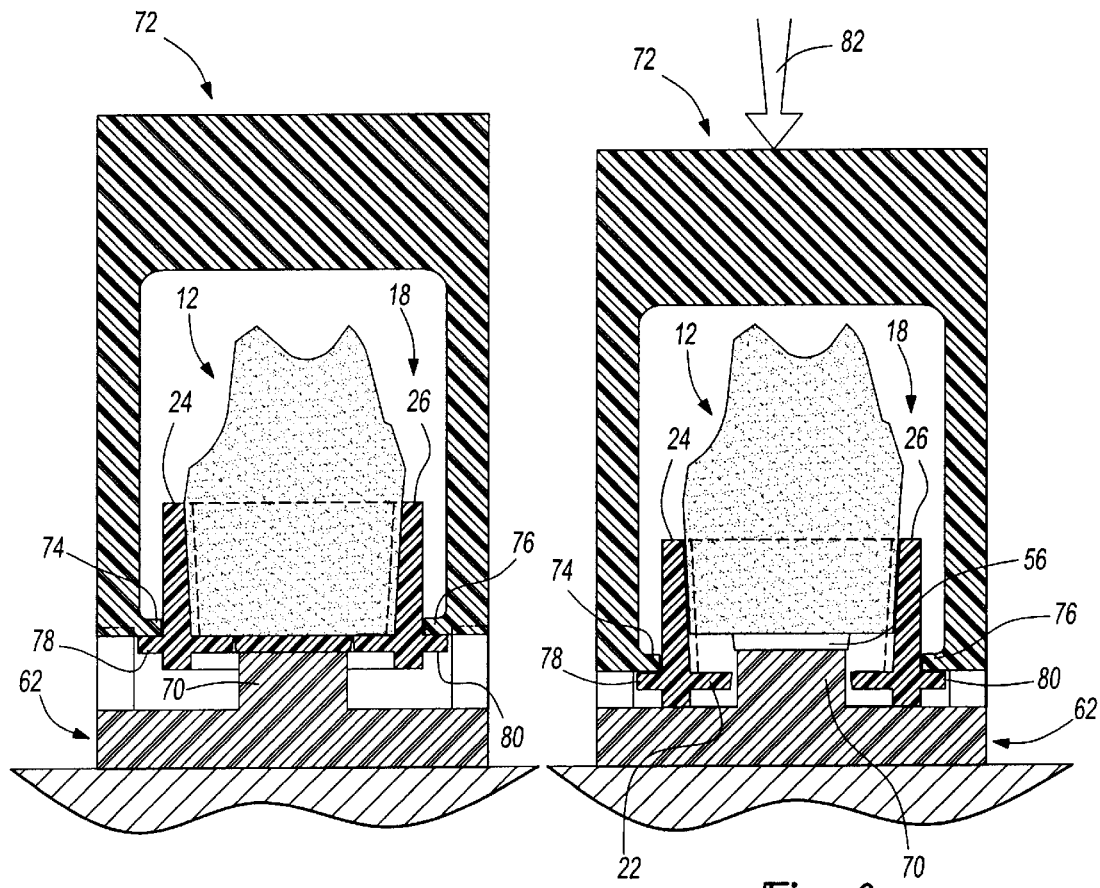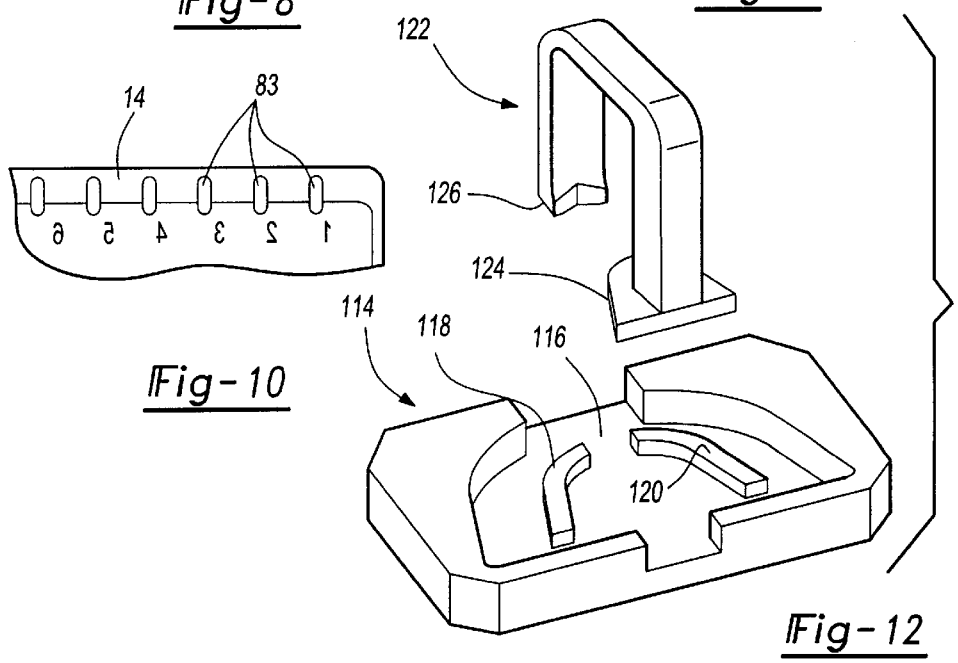

TRAY MODELING SYSTEM WITH ARTICULATOR ASSEMBLY AND EJECTION MECHANISM FOR PRODUCING A DENTAL MODEL

CROSS-REFERENCE TO APPLICATIONS

The present application is a continuation-in-part of U.S. application Ser. No. 09/133,231, filed Aug. 13, 1998 for a tray modeling system and articulator for producing a dental model.

BACKGROUND OF THE INVENTION

1. Field of the Invention

The present invention relates generally to modeling devices for mounting teeth replications made from dental impressions to create a dental model of a patient's mouth and, more particularly, to a tray modeling system with articulator assembly and ejection mechanism for producing such a dental model.

2. Description of the Prior Art

Numerous devices are known in the art for creating a working dental model of a patient's upper and lower teeth which are taken from dental impressions at the dentists office. The impression material is typically a malleable compound or a wax-type material which is molded around the patient's upper and lower teeth and gums and which creates a highly accurate negative impression of the teeth and surrounding areas. The impression is then filled with a powderized stone impression material or other appropriate material and is permitted to harden to form a highly accurate replication of the user's teeth. A series of metal dowel pins are inserted into the still hardening stone material which fills the impression at spaced intervals and correspond to the teeth or sections of teeth which are intended to be separated later on. The modeling device is normally engaged by the dowel pins to position and secure the dental impressions of the patient in such a manner so as to provide the dental professional with a highly accurate model of the user's mouth which will make possible the replication of certain of the patient's teeth in the preparation of dentures, crowns and the like.

The Vertex/KV 33 Corporation advertisement brochure teaches a dental impression model in which a powderized stone material similar to that used to create a conventional dental impression of the user's teeth is poured into an open mold. The stone material in the mold is allowed to harden to a certain degree, upon which a release spray coating is applied evenly over the exposed surface. The previously created dental impression is then immediately pressed into the mold base by engaging the dowel pins through the still somewhat malleable mold. The individual teeth or sections of teeth corresponding to the previously placed dowel pins may then be individually cut and separated from the stone base due to the release coating which prevents bonding of the hardening stone in the impression with that from the mold. The release coating allows the separated portions bonded around their respective dowel pins to be easily removed from the stone base and thus enables the specialist to begin preparing his or her model. An articulator, or universal mounting apparatus, is also employed to mount an upper impression model at a desired opposing orientation relative to a corresponding lower impression model to replicate the arrangement of the upper and lower rows of teeth.

While being fairly accurate in providing an accurate dental impression model, the Vertex model suffers from the shortcoming of being very time consuming to produce and necessitating a considerably large amount of stone substrate material, which again requires a considerable amount of setting time. An improvement of the Vertex device is taught by the Dental Ventures of America (DVA) model and die system which, in the place of a standard mold base, provides a predrilled base plate upon which the preformed dental impressions are attached. While the base plate of the DVA system reduces somewhat the time required to assemble the impression into the mold, the required time for producing the initial teeth replications from the impressions and the step of inserting the individual dowel pins into the hardening stone still largely offsets this advantage.

A marked improvement over the conventional impression models is provided by the Nu Logic E-Z Tray Model System which provides a collection of quarter and half trays which are shaped with cavities generally corresponding to the upper and lower impressions of the user's mouth and which define knurled ridges along both inwardly and outwardly facing edges which define the cavity. One or more keyed spine portions are snappingly engaged within groove shaped apertures formed in the bottom center and extending the length of the cavity. The keyed portion of the spine extends upwardly a distance into the cavity and, upon pouring of a quantity of the stone mix into the cavity, is bonded to the stone mix. The spines replace the conventional dowel pins and permit the impression and mold to be directly press fit onto the forming stone mix in the tray.

As further disclosed by the Nu Logic brochure, the model is separated from an overlaying dental impression which is press fit atop the drying stone in the base. The stone case with embedded spine may then be removed as an entire piece from the impression tray. The impression and spine may be cut by an appropriate saw into the desired sections of teeth which can then be remounted onto the tray by aligning the exterior knurled ridges of the stone case with the corresponding inwardly facing knurled ridges on the oppositely facing edges of the tray and then snapping the severed spine portions back in place along the guide slot formed in the bottom of the cavity.

U.S. Pat. No. 5,622,497, issued to Cho, discloses an improved tray system and articulator for use with a replication of a dental patient's teeth. First and second trays are provided, with each tray having a substantially planar surface upon which a substrate layer of a stone material is applied. An insert is detachably secured to each of the trays and includes an upper keyed portion around which the stone layer bonds. An upper conventional dental impression is secured to the substrate stone layer of the first dental tray and a lower dental impression is secured to the substrate layer of the second dental tray. The impression and substrate are secured to the upper and lower trays by removing the insert from within a channel formed within each tray. The channels extend around the peripheral outer portion of each tray and include first and second oppositely facing walls having rows of ridges placed thereon. Corresponding lower portions of the like configured insert are likewise provided with ridges or serrations to intermesh in an axially locating fashion at a selected point within the channel shaped tray recesses. A reusable articulator is also provided and includes first and second hinged members which secure to the first and second trays and mount the trays so as to position the teeth replications.

SUMMARY OF THE PRESENT INVENTION

The present invention is a system including first and second dental drays and an articulator for use with a conventional dental impression for creating a dental model of a patient's mouth. The tray system includes in a first preferred embodiment first and second rectangular shaped trays for holding, respectively, upper and lower dental models. Each of the trays includes a base surface, first and second spaced apart and upwardly extending side walls, and first and second end walls which define in combination recessed cavities which extend the longitudinal length of the trays. The side walls of each of the trays each further include a plurality of spaced apart and vertically extending raised portions, the purpose for which is to provide for accurate repositioning of segmented portions of a base layer of stone and secured dental model once they have been cut and removed from the tray.

Each of the base surfaces of the trays include a frangible portion formed therewith and each tray is successively set upon a template base which includes a configuration suitable for supporting the underside of the trays. A raised portion extends upwardly from the template base and corresponds in placement and outline with each of the frangible portions.

A punch member is configured to engage at least first and second selected upper surfaces of each tray and to downwardly actuate the tray so that the at least one frangible portion is forcibly disengaged from the base surface and the base layer of stone and associated dental model are ejected from within the recessed cavity.

The articulator includes first and second mounting portions extending from the first and second trays, respectively. The mounting portions include a base which supports first and second planar shaped and spaced apart guide portions for receiving therebetween first and second insert portions. The insert portions each include a plurality of horizontally disposed and alternating raised and recessed surfaces formed upon a specified planar surface which interengage in a biasing and height adjustable fashion with a further horizontally disposed and raised portion defined at an upper end of an opposing planar shaped guide portion. Pluralities of eyelet portions extend from a top of each of the insert portions and are twistingly and biasingly engaged together in a hingedly aligning fashion so as to form a common hinged axis.

In a further preferred embodiment, the trays are formed in a substantial U-shaped configuration for mounting respectively thereon a full upper half and a full lower half of a dental model. Each of the U-shaped trays includes first and second frangible portions extending along opposite sides thereof and a further configuration of the template base includes an arcuate and planar configuration having a recessed interior with first and second raised portions and which corresponds to the U-shaped configuration of the trays.

BRIEF DESCRIPTION OF THE DRAWINGS

Reference will now be had to the attached drawing, when read in combination with the following specification, wherein like reference numerals refer to like parts throughout the several views, and in which:

FIG. 1 is an exploded view in perspective of the system for creating a dental model according to a first preferred embodiment of the present invention;

FIG. 2 is a top plan view of a selected tray and illustrating the numeral inscriptions according to the present invention;

FIG. 3 is a bottom plan view of the selected tray shown in FIG. 2 and further illustrating the frangible portion according to the present invention;

FIG. 4 is a cutaway view taken along line 4—4 of FIG. 2 and illustrating a side profile of the configuration of the rectangular shaped tray according to the present invention;

FIG. 5 is view similar to FIG. 4 and further showing the base layer of stone and dental model affixed within the recessed cavity formed by the tray;

FIG. 6 is an exploded view illustrating the template base and punch member for use with the dental tray according to the first preferred embodiment for facilitating disengagement of the base layer of stone and attached dental model;

FIG. 7 is a further assembled view of the embodiment illustrated in FIG. 6 and by which the ejection of the frangible portion of the tray and the dental model is established by the downward actuation of the punch member against the tray;

FIG. 8 is a cutaway view taken along line 8—8 of FIG. 7 and illustrating the assembly prior to downward actuation of the punch member;

FIG. 9 is a view similar to FIG. 8 and illustrating the assembly subsequent to downward actuation of the punch member in which the frangible portion has been disengaged from the base surface of the tray and the dental model ejected from within the recessed cavity;

FIG. 10 is a partial sectional view of an underside of a dental impression model and which illustrates the numeral inscription thereon which corresponds with the enumeration on the inner surface of the dental tray as shown in FIG. 2 according to the present invention;

FIG. 12 is an exploded view of a template base and punch member particularly configured for use with the U-shaped tray according to the further preferred embodiment of the present invention.

DETAILED DESCRIPTION OF THE PREFERRED EMBODIMENT

Figure 11:
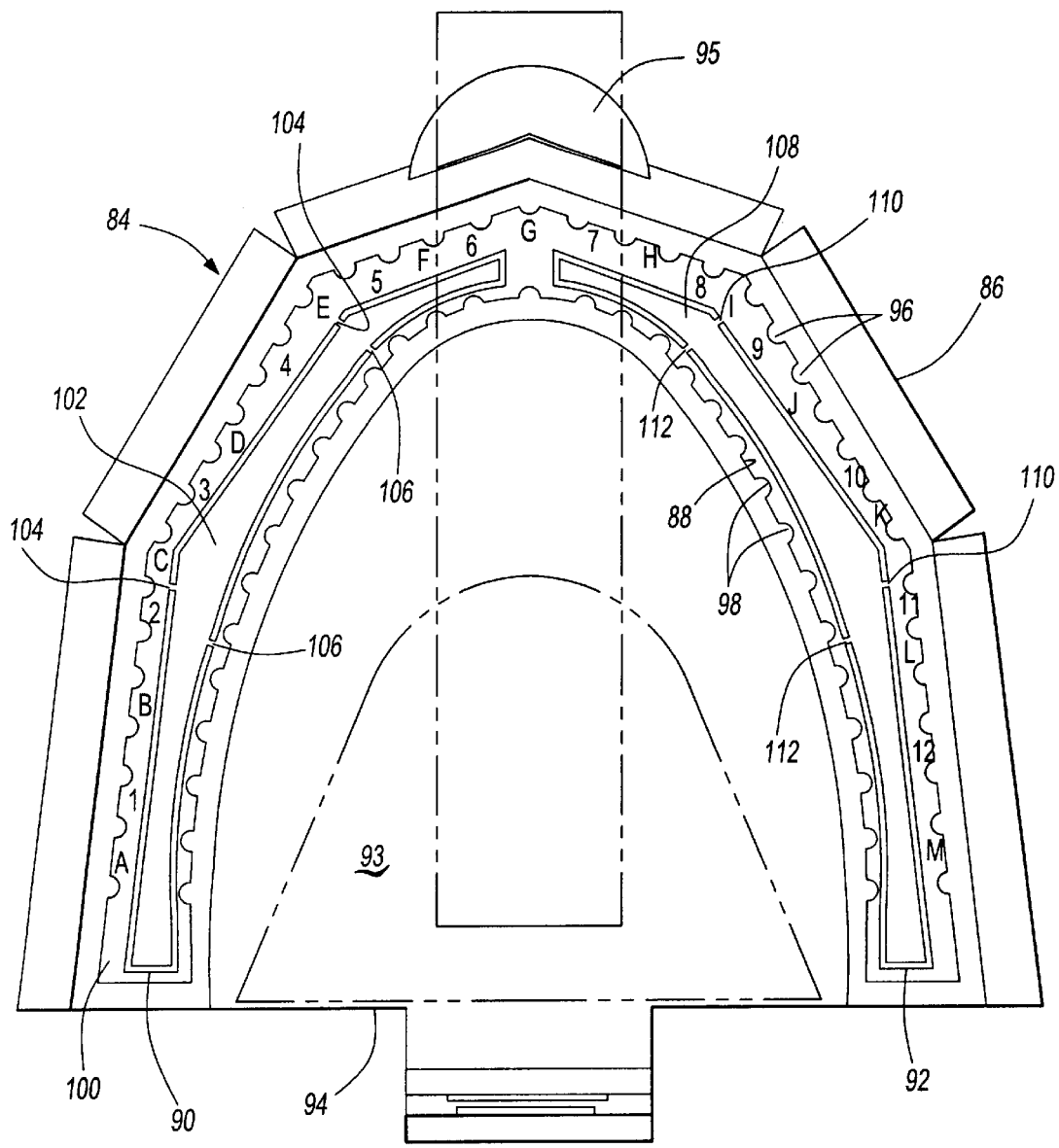
FIG. 11 is a top plan view of a selected U-shaped tray according to a further preferred embodiment of the present invention.

Referring now to FIG. 1 a system is shown at 10 according to a first preferred embodiment for mounting upper and lower dental replications produced by conventional dental impressions into a dental model of a patient's mouth. As was previously described, the taking of dental impressions at a dentists office is fairly well known in the art and normally involves fashioning a malleable and highly impressionable material such as a wax compound around the teeth and contours of the patients mouth. The dental impression is then used by a specialist along with X-rays taken by the dentist to construct a model of the patient's upper and lower teeth in a manner which will be subsequently described and as is substantially shown by dental model 12 in the side view of FIG. 5 and the exploded view of FIG. 6 which includes a base layer of stone 14 and model of teeth 16.

A first tray 18 and a second tray 20 are provided for mounting, respectively, the first and second dental models such as shown at 12. Both the first tray 18 and the second tray 20 are constructed of a polymer or like material and, as is illustrated in the first preferred embodiment, forms a generally rectangular shaped outline for mounting a quadrant (half of an upper or half of a lower) of a patient's dental model as are illustrated by dental replications. The first tray 18 includes a base surface 22, a first upwardly extending side wall 24, a second spaced apart and upwardly extending side wall 26, a first end wall 28 and a second end wall 30 which define in combination a recessed cavity extending a longitudinal length of the tray 16. Likewise, the second tray 20 includes a base surface 32, a first upwardly extending side wall 34, a second spaced apart and upwardly extending side wall 36, a first end wall 38 and a second end wall 40 and which also define in combination a recessed cavity extending a longitudinal length of the tray 18.

The side walls of the first and second trays each further include pluralities of spaced apart and vertically extending raised portions defined on inwardly facing surfaces. Specifically, side walls 24 and 26 of the first tray 18 include pluralities of spaced apart raised portions 42 and 44 while side walls 34 and 36 of the second tray 20 include pluralities of spaced apart raised portions 46 and 48. The purpose of the vertically extending raised portions 42, 44, 46 and 48 is to provide for an accurate locating means once portions of the teeth are segmented and are releasably attached to the dental model and such segmenting is illustrating by cutting lines 50, 52 and 54 in the dental model 12 of FIG. 6.

The stone material which forms the foundation of the upper and lower teeth replications is filled within the recessed cavities of the first and second trays and in turn receives thereupon the previously created dental model from the impression. The series of vertical cuts 50, 52 and 54 are made at desired locations as are shown and so as to segment the dental model 12 into individual sections. At this point any desired segmented section or sections of the dental replication is capable of being vertically removed from the tray and subsequently resecured to the tray due to the spaced apart and raised portions defined on the side surfaces of the segment which locate and reseat at the desired position relative to the raised portions defined on the interior facing surfaces of the tray side walls.

Referring to the top plan view of FIG. 2 and the bottom plan view of FIG. 3 of selected tray 18, a frangible portion 56 is shown according to the first preferred embodiment and which is formed with the base surface 22 of the tray 18. The frangible portion 56 according to the first preferred embodiment is preferably rectangular in outline corresponding with the general shape of the base surface 22 and is secured to the tray 18 by means of first 58 and second 60 pluralities of weakened portions. Referring further to the side cutaway views of FIGS. 4 and 5, the recessed cavity of the tray 18 is clearly illustrated which is capable of being filled with the stone layer 14 and upon which is affixed the teeth 16 of the dental model.

Referring now to FIGS. 6–9, an ejection mechanism is illustrated for use with the dental impression trays for facilitating disengagement of the associated dental models from within the tray and according to the present invention. Specifically, referring to FIG. 6, a template base 62 is illustrated according to the first preferred embodiment which includes a rectangular configuration corresponding with the rectangular shape of the first and second trays 18 and 20. The template base 62 is configured such that a substantially open and central surface area 64 is provided for supporting an underside of the selected tray's base surface and is centered between ends 66 and 68. A raised portion 70 is formed upon the central surface area 64 of the template base 62 and corresponds in placement and outline with the frangible portion 56 upon the selected tray, such as tray 18, being located upon the template base 62.

A punch member 72 is provided and which is configured for engaging selected locations of each of the trays, such as the tray 18, and so as to facilitate downward actuation of the tray so that the frangible portion 56 is forcibly disengaged from the base surface 22 and the base layer of stone and the associated dental model are ejected from within the recessed cavity. The punch member 72 is formed as a substantially rectangular shaped block having an internal cavity open to a bottom of the block and first and second downwardly extending sides which terminate in longitudinal edges 74 and 76. As will be further described, the internal cavity of the punch member block 72 is of sufficient dimension so as to receive therebetween the dental model 12 as shown in FIGS. 8 and 9.

The tray 18 is further characterized by opposite edge surfaces 78 and 80 which are seated by the longitudinal edges 74 and 76 of the punch 72 such that, as shown in FIG. 8, the dental tray 18 is prepared for disengagement of the model 12. As further shown in FIG. 9, a downward actuating force is illustrated at 82 so that the tray is downwardly actuated and the frangible portion 56 is forcibly disengaged from the base surface 22, with the result being that the dental model 12 is upwardly actuated a prescribed degree from the recessed interior of the cavity within the tray 18. As is further shown in FIG. 10, a bottom face of the ejected stone layer 14 includes a plurality of numeral inscriptions 83 which are formed by the opposing engravings formed upon the inner base surface of the tray as is shown in FIG. 2 and which ideally correspond with the individual teeth of the constructed dental model for assisting in section and reassembling the dental model in subsequent use.

Referring to FIGS. 11 and 12, a further preferred embodiment of the present invention is illustrated in which first and second substantially U-shaped configured trays, illustrated by tray 84, are hingedly interconnected by an articulator as will be subsequently described. The U-shaped tray 84 includes an arcuate shaped body having a first outer extending side wall 86, a second spaced apart and inner extending side wall 88, a first end wall 90 and a second end wall 92. The end walls 90 and 92 are connected along a common edge 94 of the tray 84 and the tray 84 further includes a first central upwardly facing surface area 93 at a first location and a second upper edge surface area 95 at a second location.

The first and second side walls 86 and 88 likewise include pluralities of spaced apart and vertically extending raised portions, see at 96 and 98, respectively, and the recessed cavity defined by the side and end walls further includes a base surface 100. The construction of the U-shaped dental trays is such that they are capable of supporting thereon complete upper and lower dental models (including teeth and stone substrate) in the same fashion as illustrated in the previous embodiment.

The U-shaped configured tray 84 further includes a first frangible portion 102 formed within one side of the base surface 100 and including a first plurality 104 and a second plurality 106 of weakened portions and a second frangible portion 108 formed within the opposite side of the base surface 100 and likewise including a first plurality 110 and a second plurality 112 of weakened portions. The construction of the U-shaped tray 84, similar to that of the rectangular tray 18 of the first preferred embodiment, facilitates its use with an ejection mechanism which will now be described for disengaging the stone layer and formed dental impression from within a connected and arcuate shaped cavity defined by the U-shaped tray 84.

Specifically, referring now to FIG. 12, a template base 114 according to the further preferred embodiment includes an arcuate and planar configuration having a recessed interior 116 and with first 118 and second 120 raised portions. The recessed interior 116 corresponds substantially to the U-shaped configuration of the tray 84 and the first and second raised portions 118 and 120 specifically with the frangible portions 102 and 108. A punch member 122 is substantially U shaped in the second preferred embodiment and includes a first foot supported end 124 which engages against the first surface area location 93 of the tray 84 and a second end 126 which engages against a second surface area location 95 of the tray 84. The punch member 122 operates identically to the punch block 72 described in the first preferred embodiment and so as to downwardly actuate the tray 84 within the template base 114 and so that the frangible portions 102 and 108 are forcibly disengaged by the raised portions 118 and 120 and the dental model (not shown) is forcibly ejected a selected degree from within the recessed cavity of the tray 84. The system including the U-shaped tray 84 and ejection mechanism of the second preferred embodiment therefore functions in substantially identical fashion to the system of the first preferred embodiment.

Referring again to FIG. 1, the articulator according to the present invention includes a first mounting portion 128 and a second mounting portion 130 which extend, respectively, from a selected end wall of the associated tray. In the preferred embodiment, the mounting portions 128 and 130 are integrally formed with the associated trays 18 and 20 and are constructed of a similar polymer or like material. The first mounting portion 128 includes a base 132 which supports first 134 and second 136 planar shaped and spaced apart guide portions. Likewise, the second mounting portion 130 includes a base 138 which supports first 140 and second 142 planar shaped and spaced apart guide portions.

The articulator further includes a first insert portion 144 and a second insert portion 146 which are capable of being received between the spaced apart pairs of planar shaped guide portions. Specifically, the first insert portion 144 includes a planar shaped body defined by a first planar surface 148, a second opposite facing planar surface 150 separated by a predetermined thickness, a top 152, a bottom 154, a first side 156 and a second side 158. The second insert portion 146 also includes a planar shaped body defined by a first planar surface 160, a second opposite facing planar surface 162 separated by a predetermined thickness, a top 164, a bottom 166, a first side 168 and a second side 170.

The insert portions 144 and 146 illustrated in exploded fashion in FIG. 1 further include guide portions extending from each of the first and second sides which encircle associated sides of a selected planar shaped and spaced apart guide portion. Specifically, the insert portion 144 includes angled guide portions 172 and 174 which encircle sides of the guide portion 136 of the first mounting portion 128. Correspondingly, the insert portion 146 includes identical angled guide portions 176 and 178 (hidden from view) which encircle sides of the guide portion 142 of the second mounting portion 130. Additional stabilizing portions are illustrated at 180 for first insert portion 144 (the second being hidden from view in FIG. 1) and at 182 and 184 for second insert portion 146. The purpose of the additional stabilizing portions is to assist in locating the insert portions relative to the other of the planar shaped and spaced apart guide portions. Specifically, the stabilizing portions of the first insert portion overlap sides of the second planar shaped guide portion of the first mounting portion and the stabilizing portions of the second insert portion overlap sides of the second planar shaped guide portion of the second mounting portion.

The articulator includes adjustment means established between the insert portions and the mounting portions which permit the insert portions to be raised or lowered a specified height relative to the mounting portions. The adjustment means includes a plurality of horizontally disposed and alternating raised and recessed surfaces, such as at 186 for second insert portion 146, the corresponding raised and recessed surfaces being hidden from view of the first insert portion 144 in the view of FIG. 1. The alternating raised and recessed surfaces 186 are defined upon a selected planar surface of the insert portions, such as upon surface 162 for second insert portion 146. The opposing planar surfaces of the planar shaped guide portions relative to the alternating raised and recessed surfaces include a horizontally disposed and raised portion defined at an upper end thereof and this is illustrated at 188 for planar shaped guide portion 134 and at 190 for planar shaped guide portion 140. The height of the insert portions relative to the associated trays is determined by biasingly engaging the raised portions within a selected recessed surface of the alternating raised and recessed surfaces and the range of permitted adjustment is determined by the plurality of horizontally disposed raised and recessed surfaces.

Means are further provided for hingedly securing the first insert portion 144 and the second insert portion 146 together and includes a first plurality first 192, second 194 and third 196 eyelet portions extending from the top 152 of the first insert portion 144 and which are twistingly and biasingly engaged with a second plurality of first 198, second 200 and third 202 eyelet portions extending from the top 164 of the second insert portion 146. The engagement of the pluralities of eyelet portions along a common axis permits the dental impression trays to be rotated from a substantially unfolded position as shown in the exploded view of FIG. 1 to a position in which the dental models are arranged in an opposing and arrayed manner.

The present invention according to either embodiment therefore discloses an improved system for creating a dental model and which exhibits improved height adjustment capability of the trays relative to the articulators for providing more true to scale model replications of a patients teeth. Having described my invention, additional embodiments will become apparent to those skilled in the art to which it pertains without deviating from the scope of the appended claims.

I claim:

1. A system for creating a dental model of a patient's mouth, said system comprising:

a first tray for supporting an upper dental model in an opposing and spatially arrayed fashion relative to a second tray for supporting a lower dental model, said first and second trays each including a base surface, first and second spaced apart and upwardly extending side walls and first and second end walls, said side walls each further including a plurality of spaced apart and vertically extending raised portions, said side walls and said end walls defining a recessed cavity extending substantially a longitudinal length of each of said trays and which is suitable for receiving a base layer of stone, said associated dental model being bonded to said base layer of stone;

each of said base surfaces of said first and second trays further including at least one frangible portion formed therewith;

said first and second trays each being set upon a template base, said template base including a configuration suitable for supporting an underside of each of said base surfaces and further including at least one raised portion corresponding in placement and outline with each of said frangible portions;

a punch member configured to engage at least first and second selected upper surfaces of said selected tray and to downwardly actuate said tray so that said at least one frangible portion is forcibly disengaged from said base surface and said base layer of stone and said associated dental model are ejected from within said recessed cavity;

an articulator including a first mounting portion extending from said first tray and a second mounting portion extending from said second tray, a first insert portion engaging said first mounting portion and a second insert portion engaging said second mounting portion;

hingedly securing means for pivotally connecting said first insert portion to said second insert portion; and adjustment means for establishing a height of each of said insert portions relative to said associated trays;

whereby portions of said upper and lower dental models are capable of being segmented and releasably attachable to said first and second trays in correct position due to said pluralities of raised portions, said adjustment means and said hingedly securing means providing for desired positioning of said opposingly arrayed dental models.

2. The system as described in claim 1, further comprising each of said first and second mounting portions of said articulator being integrally formed with and extending from a selected end wall of said associated tray, said mounting portions each further including a base which supports first and second planar shaped and spaced apart guide portions for receiving said insert portions therebetween.

3. The system as described in claim 2, said first and second insert portions each further comprising:

a planar shaped body capable of being received between said first and second planar shaped guide portions of each of said mounting portions, said planar shaped body including first and second planar surfaces separated by a predetermined thickness, a top, a bottom, a first side and a second side;

guide portions extending from each of said first and second sides and encircling associated sides of a selected planar shaped and spaced apart guide portion;

said adjustment means further including a selected planar surface of said insert portion being defined by a plurality of horizontally disposed and alternating raised and recessed surfaces; and an opposing planar surface of a selected and planar shaped guide portion further including a horizontally disposed and raised portion defined at an upper end thereof;

whereby said height of said insert portions relative to said associated trays is established by biasingly engaging said raised portion within a selected recessed surface of said insert portion.

4. The system as described in claim 3, said hingedly securing means further comprising a first plurality of first, second and third spaced apart eyelet portions extending from said top of said first insert portion, a second plurality of first, second and third spaced apart eyelet portions extending from said top of said second insert portion, said first and second pluralities of eyelet portions capable of being twistingly engaged in a hingedly aligning fashion so as to form a common hinged axis.

5. The system as described in claim 3, further comprising stabilizing portions extending from each of said first and second sides of said insert portions in opposite fashion relative said guide portions, said stabilizing portions overlapping associated sides of the other of said selected planar shaped and spaced apart guide portions.

6. The system as described in claim 1, said first and second trays each further comprising a rectangular shape for mounting respectively thereon an upper quadrant and a lower quadrant of a dental model, each of said rectangular shaped trays including a single frangible portion.

7. The system as described in claim 6, said template base further comprising a rectangular configuration corresponding with said rectangular shape of said first and second trays and a single raised portion, said punch member further including a substantially rectangular shaped block having an internal cavity open to the bottom and first and second downwardly extending and longitudinal edges which engage against said first and second selected upper surfaces of said rectangular shaped tray.

8. The system as described in claim 1, said first and second trays each further comprising a substantially U-shape configuration for mounting respectively thereon a full upper half and a full lower half of a dental model, each of said U-shaped halves including first and second frangible portions extending along opposite sides thereof.

9. The system as described in claim 8, said template base further comprising an arcuate and planar configuration having a recessed interior with first and second raised portions and which corresponds substantially with said U-shaped configuration of said first and second trays, said punch member further including an elongate and substantially U-shaped member having a first foot-supported end which engages against a first upper surface area of said U-shaped tray at a first location and a second end which engages against a second upper surface area of said tray at a second location.

10. The system as described in claim 1, further comprising said first and second spaced apart side walls being angularly outwardly configured in said upwardly extending direction.

11. The system as described in claim 1, further comprising an inner side of each of said base surfaces having inscribed thereupon a plurality of numerals in longitudinally extending fashion, said plurality of numerals corresponding to individual teeth of said dental model.

12. A system for creating a dental model of a patient's mouth, said system comprising:

a first tray for supporting an upper dental model in an opposing and spatially arrayed fashion relative to a second tray for supporting a lower dental model, each of said trays including side and end walls which define therebetween a recessed cavity suitable for receiving a base layer of stone, said associated dental model being bonded to said base layer of stone;

at least one frangible portion being formed within a base surface of each of said first and second trays;

a template base configured to receive a selected one of each of said first and second trays in a horizontally supported fashion, said template base including at least one raised portion corresponding in dimension and placement with said at least one frangible portion;

a punch member configured to engage first and second selected surfaces of each of said first and second trays upon setting upon said template base, said punch member downwardly actuating said selected tray so that said at least one frangible portion is forcibly disengaged from said base surface and said base layer of stone and said associated dental model are ejected from within said recessed cavity; and an articulator including first and second mounting portions extending from said first and second trays, respectively, first and second insert portions seatable within said mounting portions and including hingedly securing means for pivotally connecting said first and second trays;

whereby said articulator positions said dental model mounted to said first tray in an opposing and spatially arrayed fashion relative said dental model mounted to said second tray.

* * * * *